US010646285B2

(12) United States Patent
Siemionow et al.

(10) Patent No.: US 10,646,285 B2
(45) Date of Patent: May 12, 2020

(54) GRAPHICAL USER INTERFACE FOR A SURGICAL NAVIGATION SYSTEM AND METHOD FOR PROVIDING AN AUGMENTED REALITY IMAGE DURING OPERATION

(71) Applicant: HOLO SURGICAL INC., Chicago, IL (US)

(72) Inventors: Kris B. Siemionow, Chicago, IL (US); Cristian J. Luciano, Evergreen Park, IL (US)

(73) Assignee: HOLO SURGICAL INC., Chicago, IL (US)

( * ) Notice: Subject to any disclaimer, the term of this patent is extended or adjusted under 35 U.S.C. 154(b) by 0 days.

(21) Appl. No.: 16/059,061

(22) Filed: Aug. 9, 2018

(65) Prior Publication Data
US 2019/0053855 A1    Feb. 21, 2019

(30) Foreign Application Priority Data
Aug. 15, 2017   (EP) .................... 17186307

(51) Int. Cl.
*G02B 27/01*   (2006.01)
*G06T 7/20*    (2017.01)
(Continued)

(52) U.S. Cl.
CPC ............ *A61B 34/25* (2016.02); *A61B 5/7267* (2013.01); *A61B 34/10* (2016.02); *A61B 34/30* (2016.02);
(Continued)

(58) Field of Classification Search
CPC ......... A61B 34/25; A61B 34/10; A61B 34/30; A61B 90/37; A61B 5/7267; A61B 90/36;
(Continued)

(56) References Cited

U.S. PATENT DOCUMENTS

2005/0289472 A1 * 12/2005 Morita .................... G06F 3/011
                                                                  715/757
2006/0176242 A1   8/2006 Jaramaz et al.
(Continued)

FOREIGN PATENT DOCUMENTS

GB    2536650       9/2016
WO    20070115826   10/2007

OTHER PUBLICATIONS

JM Fitzpatrick: "The role of registration in accurate surgical guidance",Proceedings of the Institution of Mechanical Engineers, Part H: Journal of Engineering in Medicine, May 1, 2818 (2818-85-81), pp. 687-622, XP855413835, London, England DOI: 18.1243/89544119JEIM589.

*Primary Examiner* — Ke Xiao
*Assistant Examiner* — Andrew Shin
(74) *Attorney, Agent, or Firm* — Mark M. Friedman (57) ABSTRACT

Surgical navigation system: 3D display system with see-through visor; a tracking system for real-time tracking of: surgeon's head, see-through visor, patient anatomy and surgical instrument to provide current position and orientation data; a source of an operative plan, a patient anatomy data and a virtual surgical instrument model; a surgical navigation image generator to generate a surgical navigation image with a three-dimensional image representing simultaneously a virtual image of the surgical instrument corresponding to the current position and orientation of the surgical instrument and a virtual image of the surgical instrument, the see-through visor, the patient anatomy and the surgical instrument; the 3D display system configured to show the surgical navigation image at the see-through visor, such that an augmented reality image collocated with the patient anatomy in the surgical field underneath the see-
(Continued)

through visor is visible to a viewer looking from above the see-through visor towards the surgical field.

7 Claims, 10 Drawing Sheets

(51) Int. Cl.
| | | |
|---|---|---|
| *G06T 19/00* | (2011.01) | |
| *G06F 3/01* | (2006.01) | |
| *A61B 90/00* | (2016.01) | |
| *A61B 34/10* | (2016.01) | |
| *A61B 90/50* | (2016.01) | |
| *A61B 34/20* | (2016.01) | |
| *A61B 34/00* | (2016.01) | |
| *G06T 7/11* | (2017.01) | |
| *A61B 5/00* | (2006.01) | |
| *G06T 5/00* | (2006.01) | |
| *A61B 34/30* | (2016.01) | |
| *A61B 17/00* | (2006.01) | |
| *G06K 9/62* | (2006.01) | |

(52) U.S. Cl.
CPC .............. *A61B 90/36* (2016.02); *A61B 90/37* (2016.02); *G02B 27/017* (2013.01); *G02B 27/0172* (2013.01); *G06F 3/012* (2013.01); *G06F 3/013* (2013.01); *G06T 5/002* (2013.01); *G06T 7/11* (2017.01); *G06T 19/006* (2013.01); *A61B 34/20* (2016.02); *A61B 2017/00216* (2013.01); *A61B 2034/102* (2016.02); *A61B 2034/105* (2016.02); *A61B 2034/107* (2016.02); *A61B 2034/2055* (2016.02); *A61B 2034/2063* (2016.02); *A61B 2034/2068* (2016.02); *A61B 2090/363* (2016.02); *A61B 2090/365* (2016.02); *A61B 2090/367* (2016.02); *A61B 2090/368* (2016.02); *A61B 2090/3618* (2016.02); *A61B 2090/372* (2016.02); *A61B 2090/3762* (2016.02); *A61B 2090/3983* (2016.02); *A61B 2090/502* (2016.02); *G02B 2027/0134* (2013.01); *G02B 2027/0136* (2013.01); *G02B 2027/0138* (2013.01); *G02B 2027/0178* (2013.01); *G02B 2027/0187* (2013.01); *G02B 2027/0196* (2013.01); *G06K 9/6257* (2013.01); *G06K 2209/055* (2013.01); *G06T 7/20* (2013.01); *G06T 2207/10081* (2013.01); *G06T 2207/20081* (2013.01); *G06T 2207/20084* (2013.01); *G06T 2207/30012* (2013.01); *G06T 2207/30208* (2013.01); *G06T 2219/004* (2013.01)

(58) Field of Classification Search
CPC ...... A61B 2090/3983; A61B 2090/502; A61B 2034/107; A61B 2090/3618; A61B 2090/372; A61B 2090/363; A61B 2090/365; A61B 2090/368; A61B 2090/367; A61B 2034/105; A61B 34/20; A61B 2034/102; A61B 2034/2055; A61B 2034/2068; A61B 2034/2063; G06T 19/006; G06T 2207/30004; G06T 2210/41; G06T 2207/20081; G06T 7/20; G06T 2207/10081; G06T 5/002; G06T 7/11; G06T 2219/004; G06T 2207/30208; G06T 2207/30012; G06T 2207/20084; G06F 3/012; G06F 3/013; G02B 27/017; G02B 27/0172; G02B 2027/0187; G02B 2027/0134; G02B 2027/0136; G02B 2027/0196; G02B 2027/0178; G02B 2027/0138; G06K 2209/055; G06K 9/6257

See application file for complete search history.

(56) References Cited

U.S. PATENT DOCUMENTS

| | | | |
|---|---|---|---|
| 2016/0187969 A1* | 6/2016 | Larsen | .............. G06F 3/012 345/156 |
| 2016/0324580 A1 | 11/2016 | Esterberg | |
| 2017/0024903 A1 | 1/2017 | Razzaque | |
| 2017/0329402 A1* | 11/2017 | Riedel | .............. G06F 3/013 |
| 2017/0360395 A1* | 12/2017 | Razzaque | ............ A61B 8/0841 |

* cited by examiner

GRAPHICAL USER INTERFACE FOR A SURGICAL NAVIGATION SYSTEM AND METHOD FOR PROVIDING AN AUGMENTED REALITY IMAGE DURING OPERATION

TECHNICAL FIELD

The present disclosure relates to graphical user interfaces for surgical navigation systems, in particular to a system and method for operative planning and execution of a medical procedure.

BACKGROUND

Some of typical functions of a computer-assisted surgery (CAS) system with navigation include presurgical planning of a procedure and presenting preoperative diagnostic information and images in useful formats. The CAS system presents status information about a procedure as it takes place in real time, displaying the preoperative plan along with intraoperative data. The CAS system may be used for procedures in traditional operating rooms, interventional radiology suites, mobile operating rooms or outpatient clinics. The procedure may be any medical procedure, whether surgical or non-surgical.

Surgical navigation systems are used to display the position and orientation of surgical instruments and medical implants with respect to presurgical or intraoperative medical imagery datasets of a patient. These images include pre and intraoperative images, such as two-dimensional (2D) fluoroscopic images and three-dimensional (3D) magnetic resonance imaging (MRI) or computed tomography (CT).

Navigation systems locate markers attached or fixed to an object, such as surgical instruments and patient. Most commonly these tracking systems are optical and electro-magnetic. Optical tracking systems have one or more stationary cameras that observes passive reflective markers or active infrared LEDs attached to the tracked instruments or the patient. Eye-tracking solutions are specialized optical tracking systems that measure gaze and eye motion relative to a user's head. Electro-magnetic systems have a stationary field generator that emits an electromagnetic field that is sensed by coils integrated into tracked medical tools and surgical instruments.

SUMMARY OF THE INVENTION

Incorporating image segmentation processes that automatically identify various bone landmarks, based on their density, can increase planning accuracy. One such bone landmark is the spinal pedicle, which is made up of dense cortical bone making its identification utilizing image segmentation easier. The pedicle is used as an anchor point for various types of medical implants. Achieving proper implant placement in the pedicle is heavily dependent on the trajectory selected for implant placement. Ideal trajectory is identified by surgeon based on review of advanced imaging (e.g., CT or MRI), goals of the surgical procedure, bone density, presence or absence of deformity, anomaly, prior surgery, and other factors. The surgeon then selects the appropriate trajectory for each spinal level. Proper trajectory generally involves placing an appropriately sized implant in the center of a pedicle. Ideal trajectories are also critical for placement of inter-vertebral biomechanical devices.

Another example is placement of electrodes in the thalamus for the treatment of functional disorders, such as Parkinson's. The most important determinant of success in patients undergoing deep brain stimulation surgery is the optimal placement of the electrode. Proper trajectory is defined based on preoperative imaging (such as MRI or CT) and allows for proper electrode positioning.

Another example is minimally invasive replacement of prosthetic/biologic mitral valve in for the treatment of mitral valve disorders, such as mitral valve stenosis or regurgitation. The most important determinant of success in patients undergoing minimally invasive mitral valve surgery is the optimal placement of the three dimensional valve.

The fundamental limitation of surgical navigation systems is that they provide restricted means of communicating to the surgeon. Currently-available navigation systems present some drawbacks.

Typically, one or several computer monitors are placed at some distance away from the surgical field. They require the surgeon to focus the visual attention away from the surgical field to see the monitors across the operating room. This results in a disruption of surgical workflow. Moreover, the monitors of current navigation systems are limited to displaying multiple slices through three-dimensional diagnostic image datasets, which are difficult to interpret for complex 3D anatomy.

The fact that the screen of the surgical navigation system is located away from the region of interest (ROI) of the surgical field requires the surgeon to continuously look back and forth between the screen and the ROI. This task is not intuitive and results in a disruption to surgical workflow and decreases planning accuracy.

For example, a system of such type is disclosed in a U.S. Pat. No. 9,532,848, which discloses a system for assisting a user manipulating an object during a surgery, the system comprising a tracking device for tracking the object and for generating tracking data for the object and a sterilized displaying device located in a volume within the sterile field defined as being above a plane of and delimited by an operating table and below the shoulders of an operator standing next to a patient lying on the operating table, the displaying device being supported directly by the operating table. Even though the displaying device is positioned very close to the patient being operated, the surgeon still needs to look back and forth between the screen and the ROI.

When defining and later executing an operative plan, the surgeon interacts with the navigation system via a keyboard and mouse, touchscreen, voice commands, control pendant, foot pedals, haptic devices, and tracked surgical instruments. Based on the complexity of the 3D anatomy, it can be difficult to simultaneously position and orient the instrument in the 3D surgical field only based on the information displayed on the monitors of the navigation system. Similarly, when aligning a tracked instrument with an operative plan, it is difficult to control the 3D position and orientation of the instrument with respect to the patient anatomy. This can result in an unacceptable degree of error in the preoperative plan that will translate to poor surgical outcome.

There is disclosed a surgical navigation system comprising: a 3D display system with a see-through visor; a tracking system comprising means for real-time tracking of: a surgeon's head, the see-through visor, a patient anatomy and a surgical instrument to provide current position and orientation data; a source of an operative plan, a patient anatomy data and a virtual surgical instrument model; a surgical navigation image generator configured to generate a surgical navigation image comprising a three-dimensional image representing simultaneously a virtual image of the surgical instrument corresponding to the current position and orientation of the surgical instrument and a virtual image of the surgical instrument indicating the suggested positions and orientation of the surgical instrument according to the operative plan data based on the current relative position and orientation of the surgeon's head, the see-through visor, the patient anatomy and the surgical instrument; wherein the 3D display system is configured to show the surgical navigation image at the see-through visor, such that an augmented reality image collocated with the patient anatomy in the surgical field underneath the see-through visor is visible to a viewer looking from above the see-through visor towards the surgical field.

The three-dimensional image of the surgical navigation image may further comprise at least one of: the patient anatomy data, operative plan data, in accordance to the current position and orientation data provided by the tracking system.

The three-dimensional image of the surgical navigation image may further comprise a graphical cue indicating the required change of position and orientation of the surgical instrument to match the suggested position and orientation according to the pre-operative plan data.

The surgical navigation image may further comprise a set of orthogonal (axial, sagittal, and coronal) and arbitrary planes of the patient anatomy data.

The 3D display system may comprise a 3D projector and a see-through projection screen, wherein the 3D projector is configured to project the surgical navigation image onto the see-through projection screen, which is partially transparent and partially reflective, for showing the surgical navigation image.

The 3D display system may comprise a 3D projector, an opaque projection screen and a see-through mirror, wherein the 3D projector is configured to project the surgical navigation image onto the opaque projection screen for showing the surgical navigation image for emission towards the see-through mirror, which is partially transparent and partially reflective.

The 3D display system may comprise a 3D projector, a plurality of opaque mirrors, an opaque projection screen and a see-through mirror, wherein the 3D projector is configured to project the surgical navigation image towards the plurality of opaque mirrors for reflecting the surgical navigation image towards the opaque projection screen for showing the surgical navigation image for emission towards the see-through mirror, which is partially transparent and partially reflective.

The 3D display may comprise a 3D monitor for showing the surgical navigation image for emission towards the see-through mirror which is partially transparent and partially reflective.

The 3D display may comprise a see-through 3D screen, which is partially transparent and partially emissive, for showing the surgical navigation image.

The see-through visor may be configured to be positioned, when the system is in use, at a distance (d1) from the surgeon's head which is shorter than the distance (d2) from the surgical field of the patient anatomy.

The surgical navigation image generator may be controllable by an input interface comprising at least one of: foot-operable pedals, a microphone, a joystick, an eye-tracker.

The tracking system may comprise a plurality of arranged fiducial markers, including a head array, a display array, a patient anatomy array, an instrument array; and a fiducial marker tracker configured to determine in real time the positions and orientations of each of the components of the surgical navigation system.

At least one of the head array, the display array, the patient anatomy array, the instrument array may contain several fiducial markers that are not all coplanar.

There is also disclosed a method for providing an augmented reality image during an operation, comprising: providing a 3D display system with a see-through visor; providing a tracking system comprising means for real-time tracking of: a surgeon's head, the 3D see-through visor, a patient anatomy and a surgical instrument to provide current position and orientation data; providing a source of: an operative plan, a patient anatomy data and a virtual surgical instrument model; generating, by a surgical navigation image generator, a surgical navigation image comprising: a three-dimensional image representing simultaneously a virtual image of the surgical instrument corresponding to the current position and orientation of the surgical instrument and a virtual image of the surgical instrument indicating the suggested positions and orientations of the surgical instruments according to the operative plan based on the current relative position and orientation of the surgeon's head, the see-through visor, the patient anatomy and the surgical instrument; showing the surgical navigation image at the see-through visor, such that an augmented reality image collocated with the patient anatomy in the surgical field underneath the see-through visor is visible to a viewer looking from above the see-through visor towards the surgical field.

The intended use of this invention is both presurgical planning of ideal surgical instrument trajectory and placement, and intraoperative surgical guidance, with the objective of helping to improve surgical outcomes.

A combination of a navigated probe and a computer-assisted medical system is used for interactive creation of a trajectory for positioning of a medical device. A navigated probe facilitates the positioning of the medical device. The navigated probe is part of a computer-assisted medical system consisting of a 6-degree-of-freedom (DOF) tracker (optical, electromagnetic, inertial, or any other tracking technology) and a navigated structure. The navigated structure contains a graphical user interface (GUI) for displaying patient anatomy in three dimensions (3D), as well as a virtual representation of actual implanted medical devices (IMDs) and instruments during a surgical procedure in a real time.

The surgeon can control the navigated probe by looking at its virtual representation on the GUI and lining it up to the virtual representation of the organ to achieve a proper trajectory for medical implant placement. During the planning process, a virtual instrument is displayed on a 3D display device to indicate the dynamic 3D position and orientation of the medical device. The surgeon can interact with the probe and the computer-assisted medical system by either using a 6-DOF tracking device and/or by pressing on a set of pre-programmed pedals or using other input interfaces, such as a microphone (for voice commands), a joystick, an eye-tracker (for gaze tracking).

The presented system and method solve the critical problems of typical surgical navigation systems. First, they allow the surgeon to focus the visual attention to the surgical field by superimposing 3D patient anatomy, surgical guidance, and orthogonal planes directly onto the area of patient anatomy where the surgery is performed, without requiring the surgeon to look away from the surgical field. Secondly, they provide the surgeon a more intuitive mechanism to define and execute an operative plan by simply handling the surgical instruments in a 3D workspace that perfectly matches the operative field, without requiring the surgeon to perform a disorienting mental mapping of the information displayed by the navigation system to the 3D position and orientation of the surgical instruments with respect to the complex 3D anatomy. Moreover, by using the presented system and method, the time of operation can be reduced, as the more intuitive communication means do not distract the surgeon and do not require additional time to look away from the ROI.

These and other features, aspects and advantages of the invention will become better understood with reference to the following drawings, descriptions and claims.

BRIEF DESCRIPTION OF FIGURES

The surgical navigation system and method are presented herein by means of non-limiting example embodiments shown in a drawing, wherein.

DETAILED DESCRIPTION

The following detailed description is of the best currently contemplated modes of carrying out the invention. The description is not to be taken in a limiting sense, but is made merely for the purpose of illustrating the general principles of the invention.

Figure 1A:
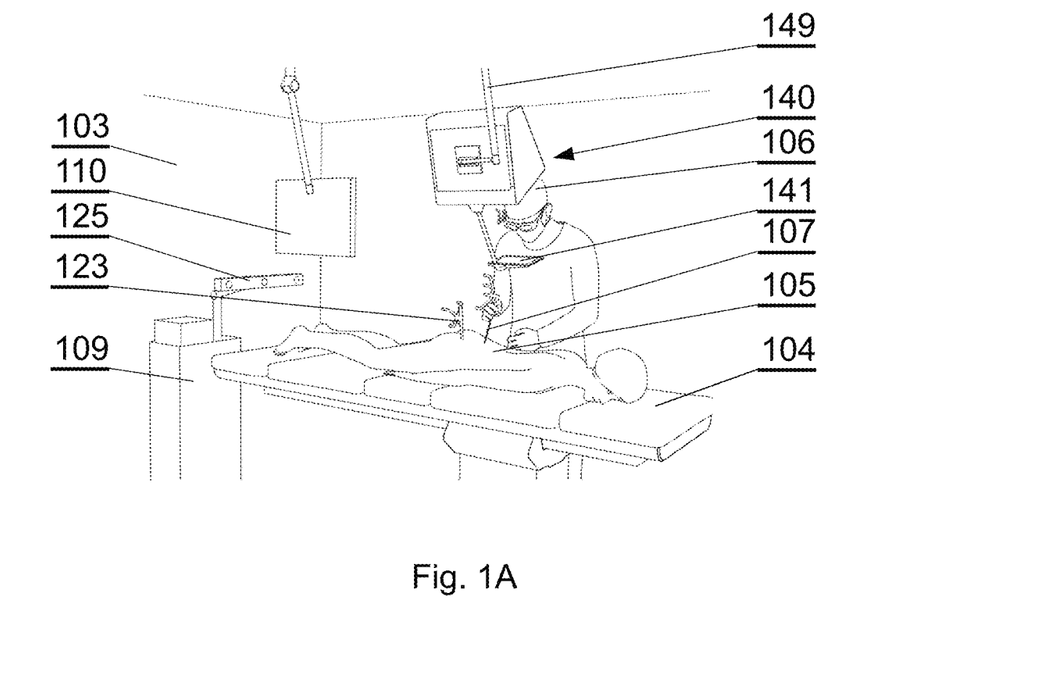
FIG. 1A shows a layout of a surgical room employing the surgical navigation system in accordance with an embodiment of the invention.
Figure 1B:
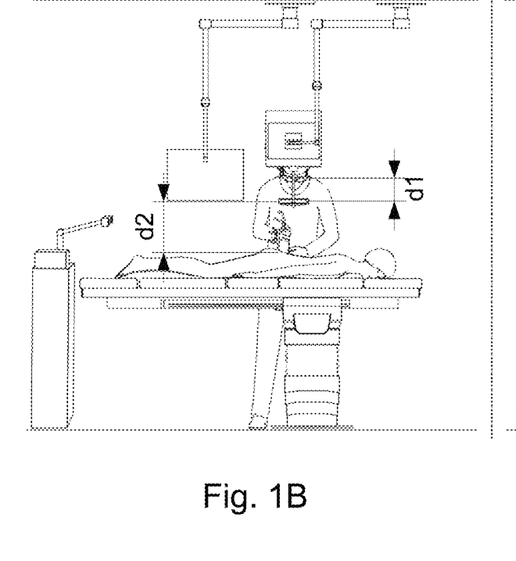
FIG. 1B shows a layout of a surgical room employing the surgical navigation system in accordance with an embodiment of the invention.
Figure 1C:
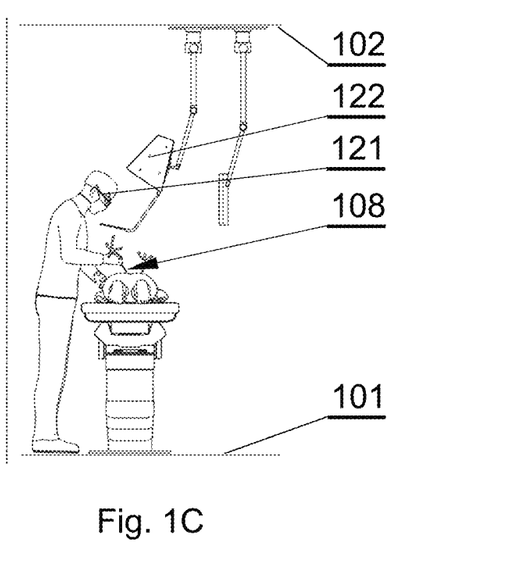
FIG. 1C shows a layout of a surgical room employing the surgical navigation system in accordance with an embodiment of the invention.

The system presented herein is comprises a 3D display system 140 to be implemented directly on real surgical applications in a surgical room as shown in FIGS. 1A-1C.

The 3D display system 140 as shown in the example embodiment comprises a 3D display 142 for emitting a surgical navigation image 142A towards a see-through mirror 141 that is partially transparent and partially reflective, such that an augmented reality image 141A collocated with the patient anatomy in the surgical field 108 underneath the see-through mirror 141 is visible to a viewer looking from above the see-through mirror 141 towards the surgical field 108.

The surgical room typically comprises a floor 101 on which an operating table 104 is positioned. A patient 105 lies on the operating table 104 while being operated by a surgeon 106 with the use of various surgical instruments 107. The surgical navigation system as described in details below can have its components, in particular the 3D display system 140, mounted to a ceiling 102, or alternatively to the floor 101 or a side wall 103 of the operating room. Furthermore, the components, in particular the 3D display system 140, can be mounted to an adjustable and/or movable floor-supported structure (such as a tripod). Components other than the 3D display system 140, such as the surgical image generator 131, can be implemented in a dedicated computing device 109, such as a stand-alone PC computer, which may have its own input controllers and display(s) 110.

In general, the system is designed for use in such a configuration wherein the distance d1 between the surgeon's eyes and the see-through mirror 141, is shorter than the distance d2, between the see-through mirror 141 and the operative field at the patient anatomy 105 being operated.

Figure 2A:
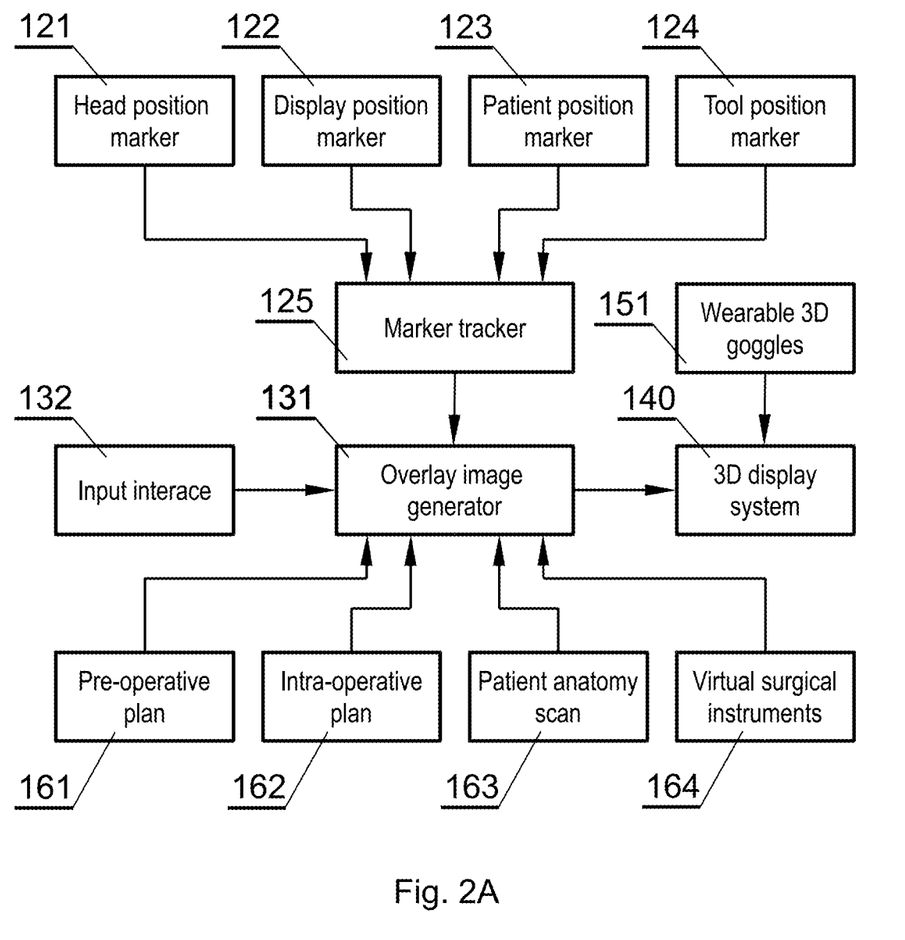
FIG. 2A shows components of the surgical navigation system in accordance with an embodiment of the invention.
Figure 2B:
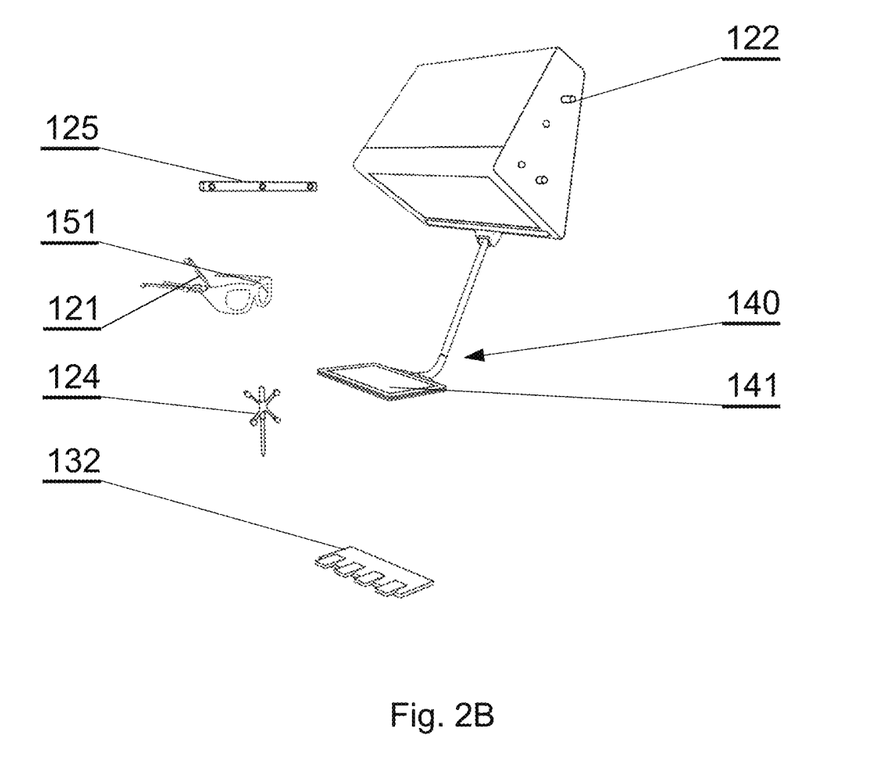
FIG. 2B shows components of the surgical navigation system in accordance with an embodiment of the invention.

FIG. 2A shows a functional schematic presenting connections between the components of the surgical navigation system and FIG. 2B shows examples of physical embodiments of various components.

The surgical navigation system comprises a tracking system for tracking in real time the position and/or orientation of various entities to provide current position and/or orientation data. For example, the system may comprise a plurality of arranged fiducial markers, which are trackable by a fiducial marker tracker 125. Any known type of tracking system can be used, for example in case of a marker tracking system, 4-point marker arrays are tracked by a three-camera sensor to provide movement along six degrees of freedom. A head position marker array 121 can be attached to the surgeon's head for tracking of the position and orientation of the surgeon and the direction of gaze of the surgeon—for example, the head position marker array 121 can be integrated with the wearable 3D glasses 151 or can be attached to a strip worn over surgeon's head.

A display marker array 122 can be attached to the see-through mirror 141 of the 3D display system 140 for tracking its position and orientation, as the see-through mirror 141 is movable and can be placed according to the current needs of the operative setup.

A patient anatomy marker array 123 can be attached at a particular position and orientation of the anatomy of the patient.

A surgical instrument marker array 124 can be attached to the instrument whose position and orientation shall be tracked.

Preferably, the markers in at least one of the marker arrays 121-124 are not coplanar, which helps to improve the accuracy of the tracking system.

Therefore, the tracking system comprises means for real-time tracking of the position and orientation of at least one of: a surgeon's head 106, a 3D display 142, a patient anatomy 105, and surgical instruments 107. Preferably, all of these elements are tracked by a fiducial marker tracker 125.

A surgical navigation image generator 131 is configured to generate an image to be viewed via the see-through mirror 141 of the 3D display system. It generates a surgical navigation image 142A comprising data representing simultaneously a virtual image 164B of the surgical instrument corresponding to the current position and orientation of the surgical instrument and a virtual image 164A of the surgical instrument indicating the suggested positions and orientation of the surgical instrument according to the operative plan data 161, 162 based on the current relative position and orientation of the surgeon's head 106, the see-through visor 141, 141B, 141D, the patient anatomy 105 and the surgical instrument 107. It may further comprise data representing the patient anatomy scan 163 (which can be generated before the operation or live during the operation).

The surgical navigation image generator 131, as well as other components of the system, can be controlled by a user (i.e. a surgeon or support staff) by one or more user interfaces 132, such as foot-operable pedals (which are convenient to be operated by the surgeon), a keyboard, a mouse, a joystick, a button, a switch, an audio interface (such as a microphone), a gesture interface, a gaze detecting interface etc. The input interface(s) are for inputting instructions and/or commands.

All system components are controlled by one or more computer which is controlled by an operating system and one or more software applications. The computer may be equipped with a suitable memory which may store computer program or programs executed by the computer in order to execute steps of the methods utilized in the system. Computer programs are preferably stored on a non-transitory medium. An example of a non-transitory medium is a non-volatile memory, for example a flash memory while an example of a volatile memory is RAM. The computer instructions are executed by a processor. These memories are exemplary recording media for storing computer programs comprising computer-executable instructions performing all the steps of the computer-implemented method according the technical concept presented herein. The computer(s) can be placed within the operating room or outside the operating room. Communication between the computers and the components of the system may be performed by wire or wirelessly, according to known communication means.

Figure 3A:
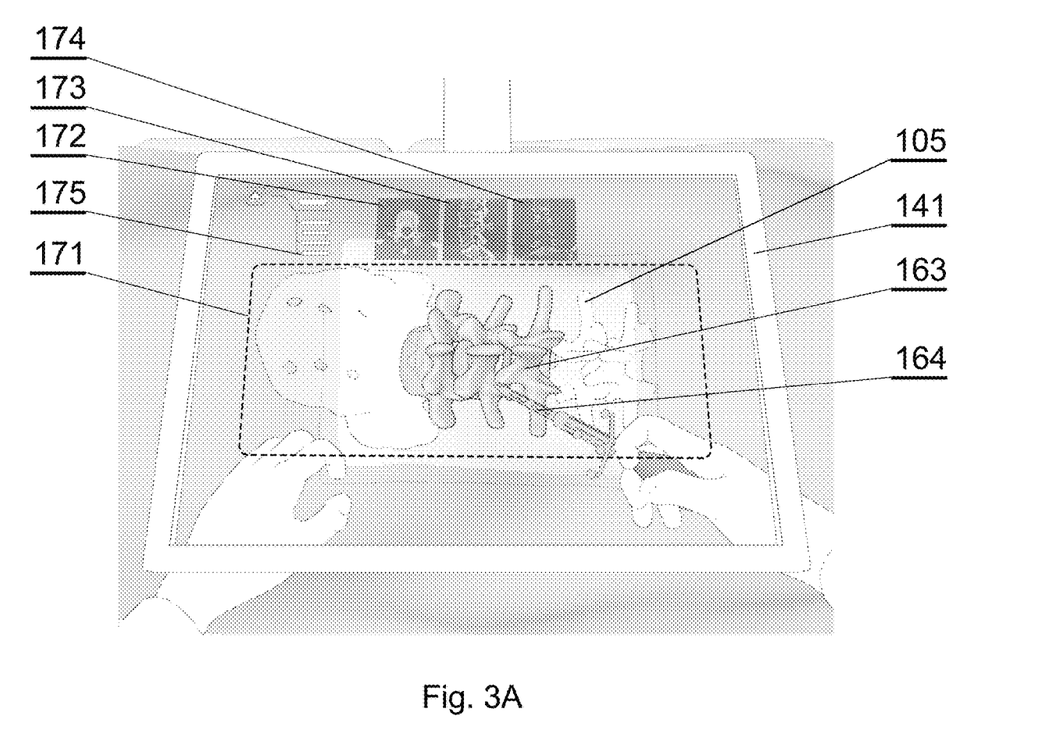
FIG. 3A shows an example of an augmented reality display in accordance with an embodiment of the invention.
Figure 3B:
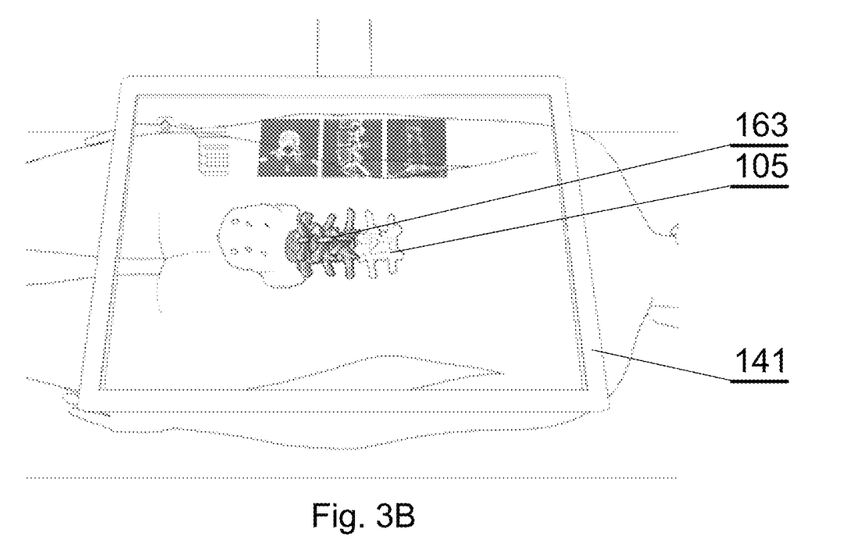
FIG. 3B shows an example of an augmented reality display in accordance with an embodiment of the invention.
Figure 3C:
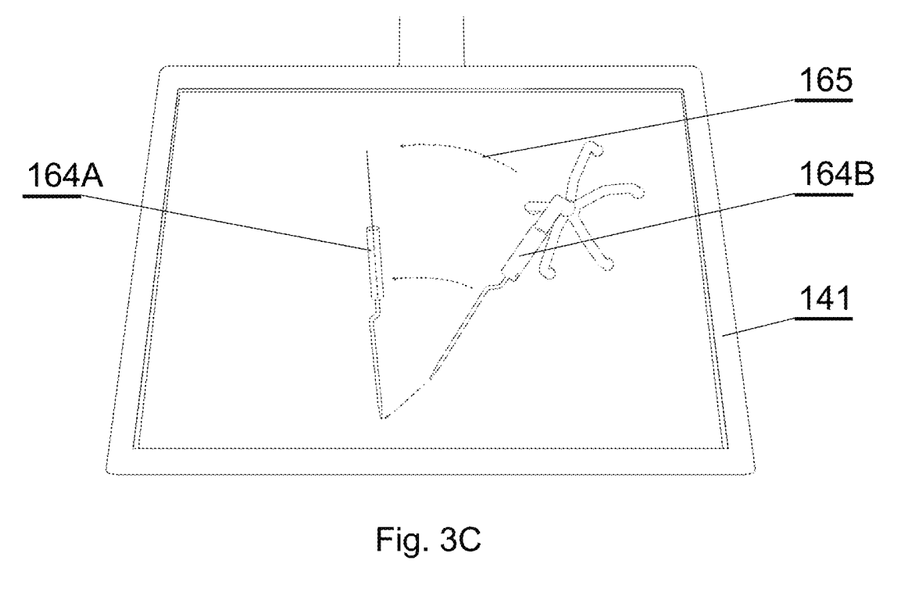
FIG. 3C shows an example of an augmented reality display in accordance with an embodiment of the invention.

The aim of the system is to generate, via the see-through visor 141, an augmented reality image such as shown in examples of FIGS. 3A-3E. When the surgeon looks via the see-through visor 141, the surgeon sees the augmented reality image 141A which comprises:

the real world image: the patient anatomy, surgeon's hands and the instrument currently in use (which may be partially inserted into the patient's body and hidden under the skin);

and a computer-generated surgical navigation image 142A comprising:

a 3D image 171 representing at least one of: the virtual image of the patient anatomy 163, the virtual image of the instrument 164 or surgical guidance indicating suggested (ideal) trajectory and placement of surgical instruments 107, according to the pre-operative plans 161 (as shown in FIG. 3C);

preferably, three different orthogonal planes of the patient anatomy data 163: coronal 174, sagittal 173, axial 172;

preferably, a menu 175 for controlling the system operation.

If the 3D display 142 is stereoscopic, the surgeon shall use a pair of 3D glasses 151 to view the augmented reality image 141A. However, if the 3D display 142 is autostereoscopic, it may be not necessary for the surgeon to use the 3D glasses 151 to view the augmented reality image 141A.

Preferably, the images of the orthogonal planes 172, 173, 174 are displayed in an area next (preferably, above) to the area of the 3D image 171, as shown in FIG. 3A, wherein the 3D image 171 occupies more than 50% of the area of the see-through visor 141.

The location of the images of the orthogonal planes 172, 173, 174 may be adjusted in real time depending on the location of the 3D image 171, when the surgeon changes the position of the head during operation, such as not to interfere with the 3D image 171.

Therefore, in general, the anatomical information of the user is shown in two different layouts that merge for an augmented and mixed reality feature. The first layout is the anatomical information that is projected in 3D in the surgical field. The second layout is in the orthogonal planes.

The surgical navigation image 142A is generated by the image generator 131 in accordance with the tracking data provided by the fiducial marker tracker 125, in order to superimpose the anatomy images and the instrument images exactly over the real objects, in accordance with the position and orientation of the surgeon's head. The markers are tracked in real time and the image is generated in real time. Therefore, the surgical navigation image generator 131 provides graphics rendering of the virtual objects (patient anatomy, surgical plan and instruments) collocated to the real objects according to the perspective of the surgeon's perspective.

For example, surgical guidance may relate to suggestions (virtual guidance clues 164) for placement of a pedicle screw in spine surgery or the ideal orientation of an acetabular component in hip arthroplasty surgery. These suggestions may take a form of animations that show the surgeon whether the placement is correct. The suggestions may be displayed both on the 3D holographic display and the orthogonal planes. The surgeon may use the system to plan these orientations before or during the surgical procedure.

In particular, the 3D image 171 is adapted in real time to the position and orientation of the surgeon's head. The display of the different orthogonal planes 172, 173, 174 may be adapted according to the current position and orientation of the surgical instruments used.

The aligning the line of sight of the surgeon onto the see-through mirror with the patient anatomy underneath the see-through mirror, involving the scaling and orientation of the image, can be realized based on known solutions in the field of computer graphics processing, in particular for virtual reality, including virtual scene generation, using well-known mathematical formulas and algorithms related to viewer centered perspective. For example, such solutions are known from various tutorials and textbooks (such as "The Future of the CAVE" by T. A. DeFanti et al, Central European Journal of Engineering, 2010, DOI: 10.2478/s13531-010-0002-5).

FIG. 3B shows an example indicating collocation of the virtual image of the patient anatomy 163 and the real anatomy 105.

For example, as shown in FIG. 3C, the 3D image 171 may demonstrate a mismatch between a supposed/suggested position of the instrument according to the pre-operative plan 161, displayed as a first virtual image of the instrument 164A located at its supposed/suggested position, and an actual position of the instrument, visible either as the real instrument via the see-through display and/or a second virtual image of the instrument 164B overlaid on the current position of the instrument. Additionally, graphical guiding cues, such as arrows 165 indicating the direction of the supposed change of position, can be displayed.

Figure 3D:
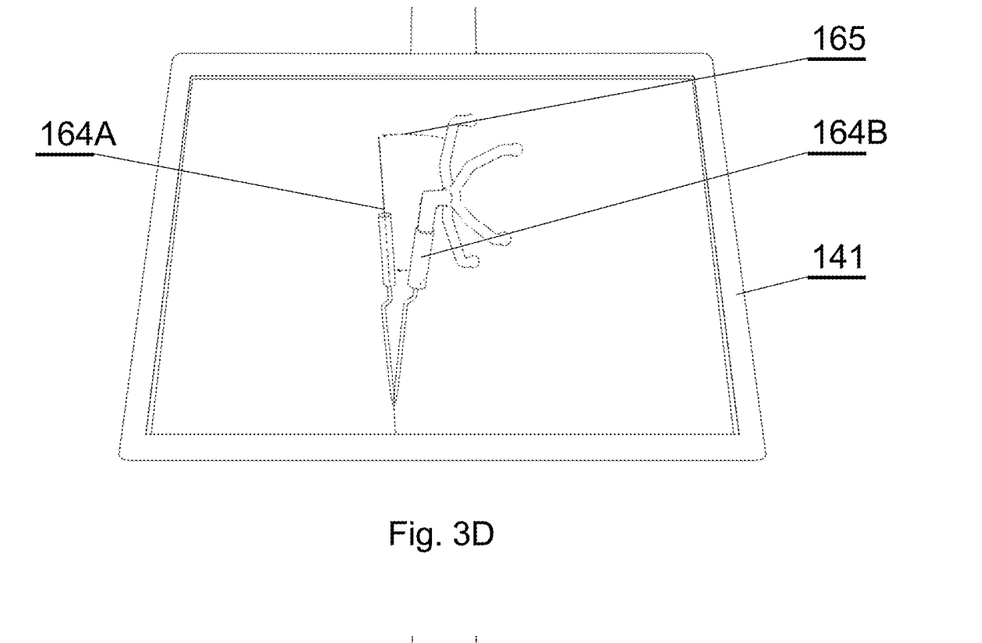
FIG. 3D shows an example of an augmented reality display in accordance with an embodiment of the invention.

FIG. 3D shows a situation wherein the tip of the supposed position of the instrument displayed as the first virtual image 164A according to the pre-operative plan 161 matches the tip of the real surgical instrument visible or displayed as the second virtual image 164B. However, the remainder of objects do not match, therefore the graphical cues 165 still indicate the need to change position. The surgical instrument is close to the correct position and the system may provide information on how close the surgical instrument is to the planned position.

Figure 3E:
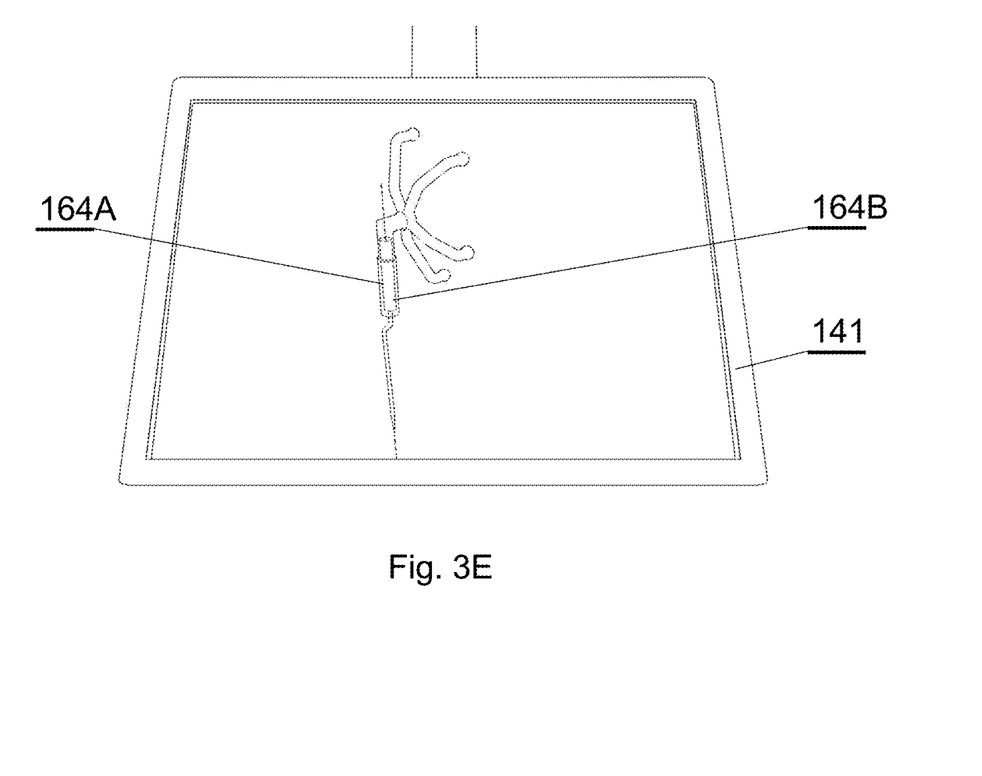
FIG. 3E shows an example of an augmented reality display in accordance with an embodiment of the invention.

FIG. 3E shows a situation wherein the supposed position of the real surgical instrument matches the position of the instrument according to the pre-operative plan 161, i.e. the correct position for surgery. In this situation the graphical cues 165 are no longer displayed, but the virtual images 164A, 164B may be changed to indicate the correct position, e.g. by highlighting it or blinking.

The see-through mirror (also called a half-silvered mirror) 141 is at least partially transparent and partially reflective, such that the viewer can see the real world behind the mirror but the mirror also reflects the surgical navigation image generated by the display apparatus located above it.

For example, a see-through mirror as commonly used in teleprompters can be used. For example, the see-through mirror 141 can have a reflective and transparent rate of 50 R/50 T, but other rates can be used as well.

The surgical navigation image is emitted from above the see-through mirror 141 by the 3D display 142.

Figure 4A:
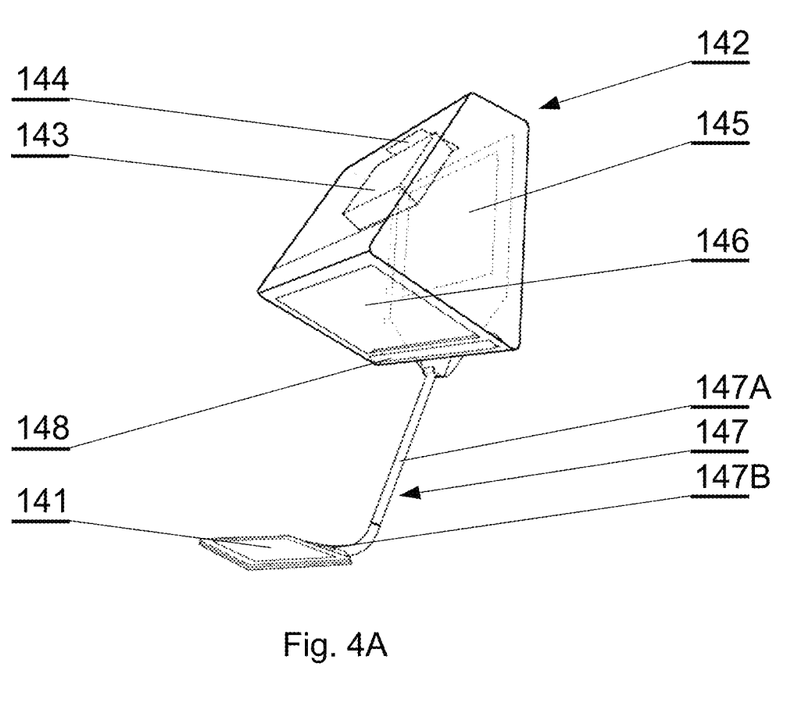
FIG. 4A shows an embodiment of a 3D display system.
Figure 4B:
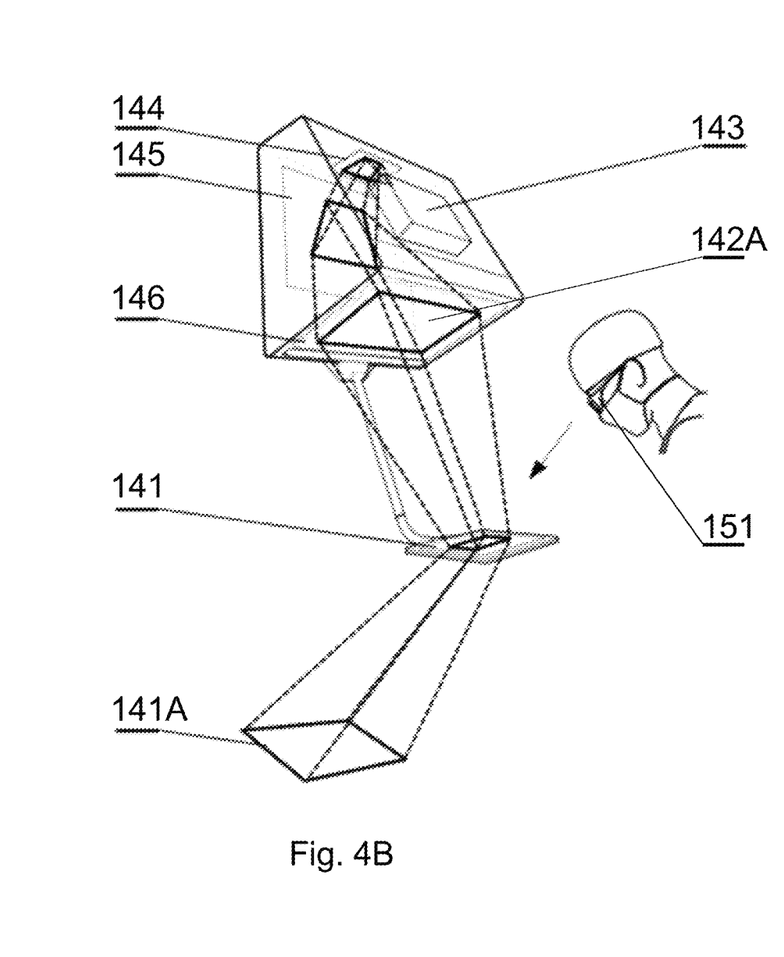
FIG. 4B shows another embodiment of a 3D display system.

In an example embodiment as shown in FIGS. 4A and 4B, a special design of the 3D display 142 is provided that is compact in size to facilitate its mounting within a limited space at the operating room. That design allows generating images of relatively large size, taking into account the small distance between the 3D display 142 and the see-through mirror 141, without the need to use wide-angle lens that could distort the image.

The 3D display 142 comprises a 3D projector 143, such as a DLP projector, that is configured to generate an image, as shown in FIG. 4B (by the dashed lines showing image projection and solid lines showing images generated on particular reflective planes). The image from the 3D projector 143 is firstly refracted by an opaque top mirror 144, then it is refracted by an opaque vertical mirror 145 and subsequently placed on the correct dimensions on a projection screen 146 (which can be simply a glass panel). The projection screen 146 works as a rear-projection screen or a small bright 3D display. The image displayed at the projection screen 146 is reflected by the see-through mirror 141 which works as an augmented reality visor. Such configuration of the mirrors 144, 145 allows the image generated by the 3D projector 143 to be shown with an appropriate size at the projection screen 146. The fact that the projection screen 146 emits an enlarged image generated by the 3D projector 143 makes the emitted surgical navigation image bright, and therefore well visible when reflected at the see-through mirror 141. Reference 141A indicates the augmented reality image as perceived by the surgeon when looking at the see-through mirror 141.

The see-through mirror 141 is held at a predefined position with respect to the 3D projector 143, in particular with respect to the 3D projector 143, by an arm 147, which may have a first portion 147A fixed to the casing of the 3D display 142 and a second portion 147B detachably fixed to the first portion 147A. The first portion 147A may have a protective sleeve overlaid on it. The second portion 147B, together with the see-through mirror 141, may be disposable in order to keep sterility of the operating room, as it is relatively close to the operating field and may be contaminated during the operation. The arm can also be foldable upwards to leave free space of the work space when the arm and augmented reality are not needed.

Figure 4C:
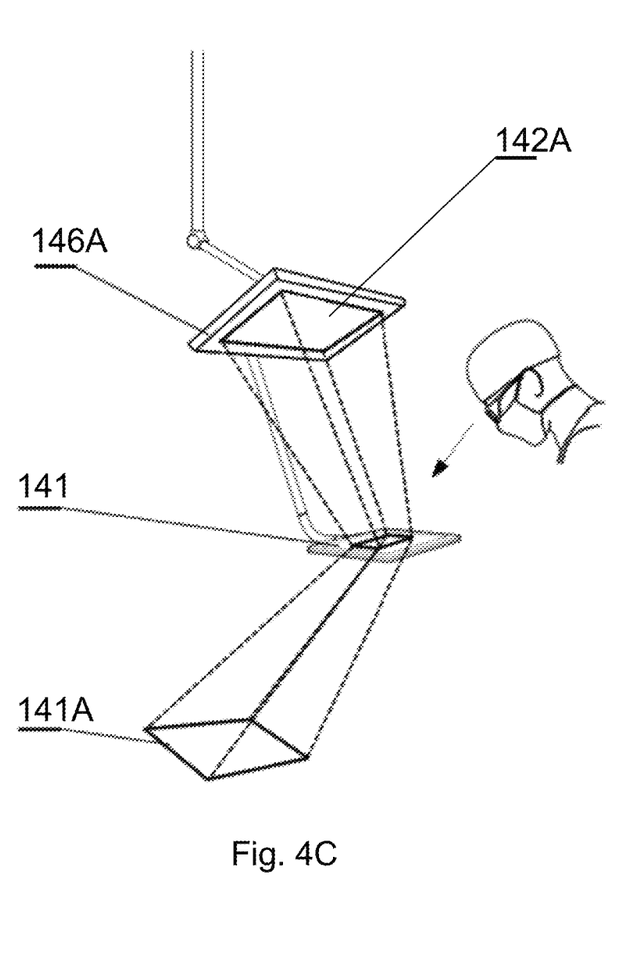
FIG. 4C shows another embodiment of a 3D display system.
Figure 4D:
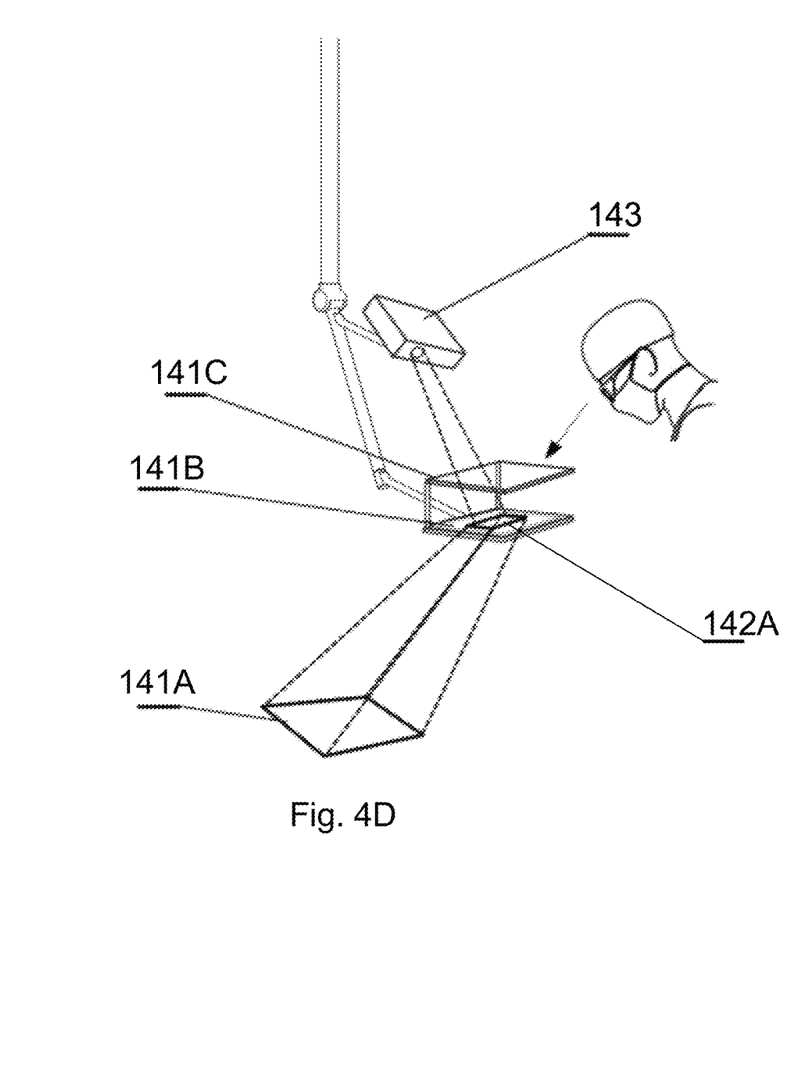
FIG. 4D shows another embodiment of a 3D display system.
Figure 4E:
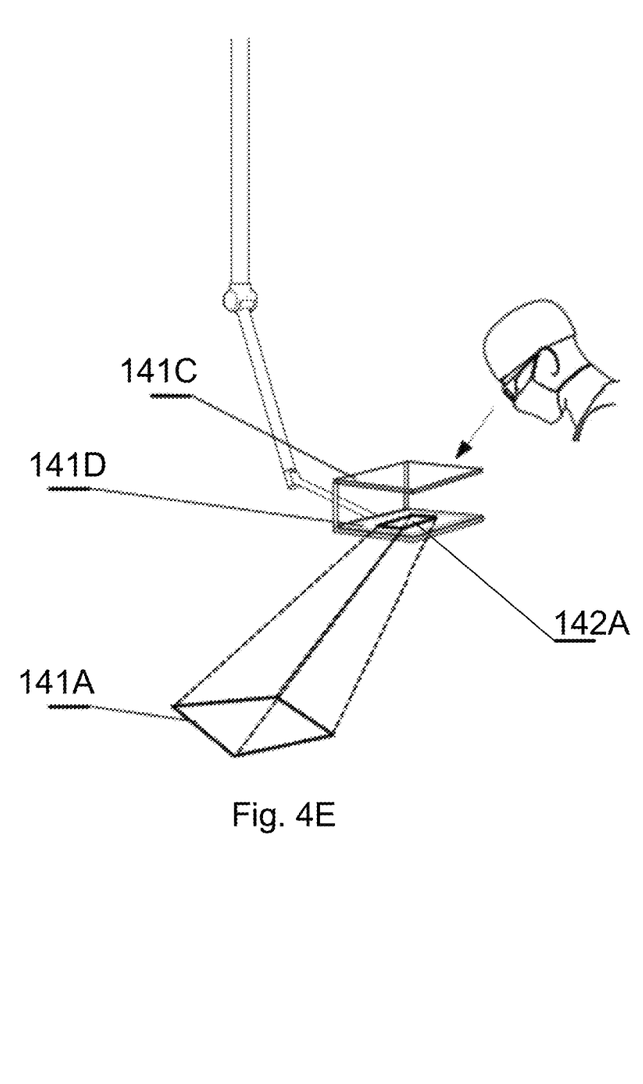
FIG. 4E shows another embodiment of a 3D display system.

In alternative embodiments, as shown for example in FIGS. 4C, 4D, 4E, alternative devices may be used in the 3D display system 140 in place of the see-through mirror 141 and the 3D display 142.

As shown in FIG. 4C, a 3D monitor 146A can be used directly in place of the projection screen 146.

As shown in FIG. 4D, a 3D projector 143 can be used instead of the 3D display 142 of FIG. 4A, to project the surgical navigation image onto a see-through projection screen 141B, which is partially transparent and partially reflective, for showing the surgical navigation image 142A and allowing to see the surgical field 108. A lens 141C can be used to provide appropriate focal position of the surgical navigation image.

As shown in FIG. 4E, the surgical navigation image can be displayed at a three-dimensional see-through screen 141D and viewed by the user via a lens 141C used to provide appropriate focal position of the surgical navigation image.

Therefore, see-through screen 141B, the see-through display 141D and the see-through mirror 141 can be commonly called a see-through visor.

If a need arises to adapt the position of the augmented reality screen with respect to the surgeon's head (for example, to accommodate the position depending on the height of the particular surgeon), the position of the whole 3D display system 140 can be changed, for example by manipulating an adjustable holder (a surgical boom) 149 on FIG. 1A, by which the 3D display 142 is attachable to an operating room structure, such as a ceiling, a wall or a floor.

Figure 5A:
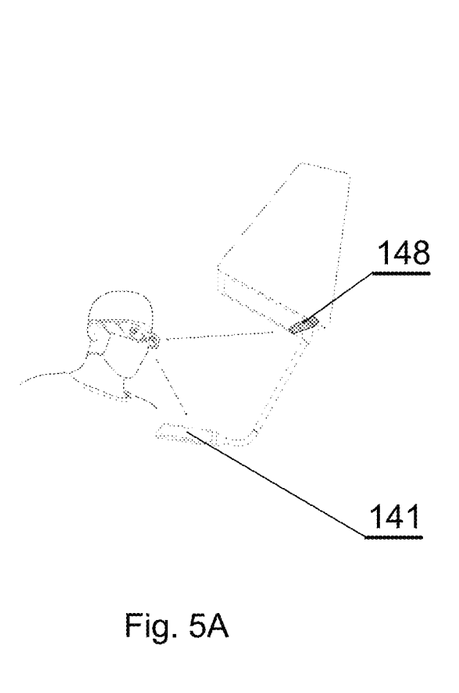
FIG. 5A show eye tracking in accordance with an embodiment of the invention.
Figure 5B:
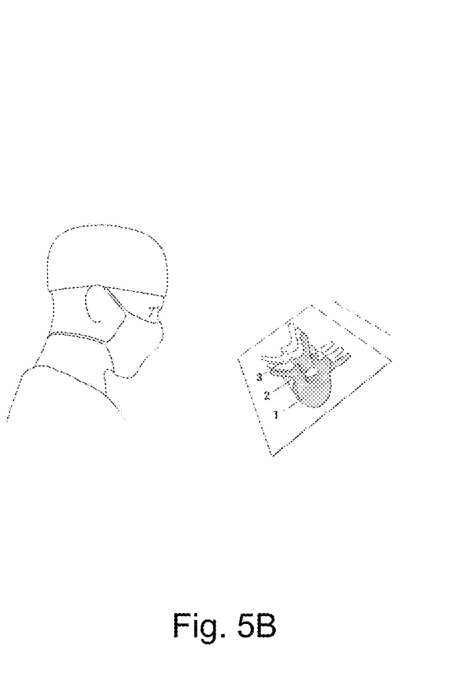
FIG. 5B show eye tracking in accordance with an embodiment of the invention.

An eye tracker 148 module can be installed at the casing of the 3D display 142 or at the see-through visor 141 or at the wearable glasses 151, to track the position and orientation of the eyes of the surgeon and input that as commands via the gaze input interface to control the display parameters at the surgical navigation image generator 131, for example to activate different functions based on the location that is being looked at, as shown in FIGS. 5A and 5B.

For example, the eye tracker 148 may use infrared light to illuminate the eyes of the user without affecting the visibility of the user, wherein the reflection and refraction of the patterns on the eyes are utilized to determine the gaze vector (i.e. the direction at which the eye is pointing out). The gaze vector along with the position and orientation of the user's head is used to interact with the graphical user interface. However, other eye tracking algorithms techniques can be used as well.

It is particularly useful to use the eye tracker 148 along with the pedals 132 as the input interface, wherein the surgeon may navigate the system by moving a cursor by eye sight and inputting commands (such as select or cancel) by pedals.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:
1. A surgical navigation system comprising:
   a 3D display system with a see-through visor;

a tracking system comprising means for real-time tracking of: a surgeon's head, the see-through visor, a patient anatomy and a surgical instrument to provide current position and orientation data;

a source of an operative plan, a patient anatomy data and a virtual surgical instrument model;

a surgical navigation image generator configured to generate a surgical navigation image comprising a three-dimensional image representing simultaneously a virtual image of the surgical instrument corresponding to the current position and orientation of the surgical instrument and a virtual image of the surgical instrument indicating the suggested positions and orientation of the surgical instrument according to the operative plan data based on the current relative position and orientation of the surgeon's head, the see-through visor, the patient anatomy and the surgical instrument;

wherein the 3D display system is configured to show the surgical navigation image at the see-through visor, such that an augmented reality image collocated with the patient anatomy in the surgical field underneath the see-through visor is visible to a viewer looking from above the see-through visor towards the surgical field, wherein the 3D display system comprises a 3D projector, a plurality of opaque mirrors, an opaque projection screen and a see-through mirror, wherein the 3D projector is configured to project the surgical navigation image towards the plurality of opaque mirrors for reflecting the surgical navigation image towards the opaque projection screen for showing the surgical navigation image for emission towards the see-through mirror, which is partially transparent and partially reflective.

2. The system of claim 1, wherein the three-dimensional image of the surgical navigation image further comprises at least one of: the patient anatomy data, operative plan data, in accordance to the current position and orientation data provided by the tracking system.

3. The system of claim 1, wherein the three-dimensional image of the surgical navigation image further comprises a graphical cue indicating the required change of position and orientation of the surgical instrument to match the suggested position and orientation according to the pre-operative plan data.

4. The system of claim 1, wherein the surgical navigation image further comprises a set of orthogonal (axial, sagittal, and coronal) and arbitrary planes of the patient anatomy data.

5. The system of claim 1, wherein the 3D display system comprises a 3D projector and a see-through projection screen, wherein the 3D projector is configured to project the surgical navigation image onto the see-through projection screen, which is partially transparent and partially reflective, for showing the surgical navigation image.

6. The system of claim 1, wherein the 3D display system comprises a 3D projector, an opaque projection screen and a see-through mirror, wherein the 3D projector is configured to project the surgical navigation image onto the opaque projection screen for showing the surgical navigation image for emission towards the see-through mirror, which is partially transparent and partially reflective.

7. A method for providing an augmented reality image during an operation, comprising:

providing a 3D display system with a see-through visor;

providing a tracking system comprising means for real-time tracking of: a surgeon's head, the 3D see-through visor, a patient anatomy and a surgical instrument to provide current position and orientation data;

providing a source of: an operative plan, a patient anatomy data and a virtual surgical instrument model;

generating, by a surgical navigation image generator, a surgical navigation image comprising:

a three-dimensional image representing simultaneously a virtual image of the surgical instrument corresponding to the current position and orientation of the surgical instrument and a virtual image of the surgical instrument indicating the suggested positions and orientations of the surgical instruments according to the operative plan based on the current relative position and orientation of the surgeon's head, the see-through visor, the patient anatomy and the surgical instrument;

showing the surgical navigation image at the see-through visor, such that an augmented reality image collocated with the patient anatomy in the surgical field underneath the see-through visor is visible to a viewer looking from above the see-through visor towards the surgical field, wherein the 3D display system comprises a 3D projector, a plurality of opaque mirrors, an opaque projection screen and a see-through mirror, wherein the 3D projector is configured to project the surgical navigation image towards the plurality of opaque mirrors for reflecting the surgical navigation image towards the opaque projection screen for showing the surgical navigation image for emission towards the see-through mirror, which is partially transparent and partially reflective.

* * * * *